(12) United States Patent
Fang et al.

(10) Patent No.: US 12,404,333 B2
(45) Date of Patent: Sep. 2, 2025

(54) ANTI PD-L1 ANTIBODY AND USE THEREOF

(71) Applicant: REMEGEN CO., LTD., Shandong (CN)

(72) Inventors: Jianmin Fang, Shandong (CN); Jing Jiang, Shandong (CN); Shenjun Li, Shandong (CN); Guorui Zhao, Shandong (CN)

(73) Assignee: REMEGEN CO., LTD., Shandong (CN)

( * ) Notice: Subject to any disclaimer, the term of this patent is extended or adjusted under 35 U.S.C. 154(b) by 1091 days.

(21) Appl. No.: 17/312,884

(22) PCT Filed: Aug. 25, 2020

(86) PCT No.: PCT/CN2020/110935
§ 371 (c)(1),
(2) Date: Jun. 10, 2021

(87) PCT Pub. No.: WO2021/037007
PCT Pub. Date: Mar. 4, 2021

(65) Prior Publication Data
US 2022/0177590 A1    Jun. 9, 2022

(30) Foreign Application Priority Data

Aug. 29, 2019   (CN) .......................... 201910805440.7

(51) Int. Cl.
| | | |
|---|---|---|
| *C12N 15/63* | (2006.01) | |
| *A61K 39/00* | (2006.01) | |
| *A61P 35/00* | (2006.01) | |
| *C07K 16/28* | (2006.01) | |
| *C12N 15/62* | (2006.01) | |

(52) U.S. Cl.
CPC .......... *C07K 16/2827* (2013.01); *A61P 35/00* (2018.01); *A61K 2039/505* (2013.01); *C07K 2317/24* (2013.01); *C07K 2317/76* (2013.01); *C07K 2317/92* (2013.01); *C12N 15/62* (2013.01); *C12N 15/63* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 9,334,331 B2 * | 5/2016 | Igawa | ..................... | C07K 16/36 |
| 10,421,807 B2 * | 9/2019 | Gonzales | ................ | A61P 17/08 |
| 2019/0083644 A1 | 3/2019 | Yoo et al. | | |

FOREIGN PATENT DOCUMENTS

| | | |
|---|---|---|
| CA | 3137211 A1 | 9/2021 |
| CN | 104470949 A | 3/2015 |
| CN | 109195991 A | 1/2019 |
| CN | 109232740 A | 1/2019 |
| CN | 109627338 A | 4/2019 |
| EP | 3378871 A1 | 9/2018 |
| EP | 3470429 A1 | 4/2019 |
| EP | 3858862 A1 | 8/2021 |
| JP | 2018-536401 A | 12/2018 |
| RU | 2523894 C2 | 7/2014 |
| RU | 2580045 C2 | 4/2016 |
| TW | 201620936 A | 6/2016 |
| WO | WO 2007/005874 A2 | 1/2007 |
| WO | WO 2017/020858 A1 | 2/2017 |
| WO | WO 2017/058859 A1 | 4/2017 |
| WO | WO 2017/132562 A1 | 8/2017 |
| WO | WO 2017/220990 A1 | 12/2017 |
| WO | WO 2018/052818 A1 | 3/2018 |
| WO | WO 2019/129211 A1 | 7/2019 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331 -1342).*
Rabia et al. (2018, Biochemical Engineering Journal 137:365-374).*
Gura (Science, v278, 1997, pp. 1041-1042).*
Freshney (Culture of Animal Cells, A Manual of Basic Technique, Alan R. Liss, Inc., 1983, New York, p. 4).*
Zips et al. (2005, In Vivo 19:1-8).*
Editorial, (2013, Nature Biotechnology 31:85).*
International Search Report in PCT/CN2020/110935 mailed Dec. 2, 2020.
Chen, L and Flies, D B., "Molecular mechanisms of T cell co-stimulation and co-inhibition", Nature Reviews Immunology, 2013, 13(4): 227-242.
Ohaegbulam, K C et al., "Human cancer immunotherapy with antibodies to the PD-1 and PD-L1 pathway," Trends in Molecular Medicine, 2015, 21(1): 24-33.
Ishida, M et al., "Differential expression of PD-L1 and PD-L2, ligands for an inhibitory receptor PD-1, in the cells of lymphohematopoietic tissues," Immunology Letters, 2002, 84(1): 57-62.

(Continued)

*Primary Examiner* — Elizabeth C. Kemmerer
(74) *Attorney, Agent, or Firm* — Knobbe, Martens, Olson & Bear, LLP (57) ABSTRACT

Provided in the present invention is a PD-L1 immunosuppressant, and specifically provided are a monoclonal antibody capable of targeting PD-L1, and nucleotides, combinations of polynucleotides, expression vectors and combinations of expression vectors encoding the antibody. Also provided in the present invention is a conjugate or pharmaceutical composition containing the above-mentioned anti PD-L1 antibody. Further provided in the present invention is the use of the above-mentioned anti PD-L1 antibody, nucleotides, combinations of polynucleotides, expression vectors, combinations of expression vectors, conjugate or pharmaceutical composition in the preparation of a medicament for treating or preventing cancers.

12 Claims, 3 Drawing Sheets

Specification includes a Sequence Listing.

(56) References Cited

OTHER PUBLICATIONS

Taube, J M et al., "Colocalization of inflammatory response with B7-h1 expression in human melanocytic lesions supports an adaptive resistance mechanism of immune escape", Science Translational Medicine, 2012, 4(127): 127ra37.

Tseng, S Y et al., "B7-DC, a new dendritic cell molecule with potent costimulatory properties for T cells," The Journal of Experimental Medicine, 2001, 193(7): 839-845.

Butte, M J et al., "Programmed death-1 ligand 1 interacts specifically with the B7-1 costimulatory molecule to inhibit T cell responses," Immunity, 2007, 27(1): 111-122.

Cheng X et al., "Structure and interactions of the human programmed cell death 1 receptor," The Journal of Biological Chemistry, 2013, 288(17): 11771-11785.

Dirix, Luc Y., "Avelumab, an anti-PD-L1 antibody, in patients with locally advanced or metastatic breast cancer: a phase 1b JAVELIN Solid Tumor Study", Breast Cancer Res Treat (2018) 167:671-686.

Boyerinas, Benjamin, et al., "Antibody-dependent cellular cytotoxicity (ADCC) activity of a novel anti-PD-L1 antibody avelumab (MSB0010718C) on human tumor cells," Cancer Immunol Res. Oct. 2015; 3(10): 1148-1157.

Liu, An, "Discovery on small molecular inhibitors of PD-1/PD-L1 pathway", Jilin: Jilin University School of Pharmaceutical Sciences, 2016, (in 77 pages).

European Search Report received in European Application No. 20859087.7 dated Jun. 13, 2022 in 9 pages.

Japanese Office Action received in Japanese Application No. 2021-549665 dated Aug. 18, 2022 in 14 pages.

Russian Office Action in Russian Patent Application No. 2021108266 issued Jan. 21, 2022.

Pakula, Andrew A., et al., "Genetic Analysis of Protein Stability and Function," Annual Rev. Genet. 1989, 23:289-310.

\* cited by examiner

ANTI PD-L1 ANTIBODY AND USE THEREOF

FIELD

The present invention relates to the field of biomedicine, specifically to an anti-PD-L1 antibody or antigen-binding fragment thereof, and medical use thereof.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 35124494_1.TXT, the date of creation of the ASCII text file is Jun. 10, 2021, and the size of the ASCII text file is 14,066 bytes.

BACKGROUND

Recently, in the field of tumor therapy, increasing efforts have been dedicated to utilizing the body's immune system to defense tumors. This method of inhibition and killing of tumor cells by mobilizing the body's immune system is called as tumor immunotherapy. Tumor immunotherapy, including cell immunotherapy, tumor vaccines, passive immunotherapy targeting tumors, and immune checkpoint inhibitors, is currently the most promising research direction in the field of tumor therapy and has yielded a number of prospective research results.

Immune checkpoint refers to a signaling pathway that controls the intensity of T cell immune response by balancing costimulatory and co-suppressive signals (Reference 1). Immune checkpoints can maintain immune tolerance by regulating the intensity of the autoimmune response under normal circumstances. When the body is invaded by tumors, however, the activation of immune checkpoints can inhibit autoimmunity, which favors the growth and escape of tumor cells. Immune checkpoints such as CTLA-4, programmed death receptor-1 (PD-1)/programmed death ligand-1 (PD-L1) and TIM-3 are the key negatively regulatory molecules, playing an important role in tumors' immune evasion. Blocking the negatively regulatory pathway of immune checkpoints with a specific antibody and rebuilding the ability of body's immune system to recognize and kill tumor cells have achieved good therapeutic outcomes in tumor immunotherapy.

Among the known immune checkpoints, PD-1/PD-L1 has drawn high attention in tumor immune the anti-PD-L1 antibody or antigen-binding fragment to be expressed, and recovering the antibody or fragment.

The present invention further provides a method for enhancing T cell function, comprising administering an effective amount of the above-mentioned pharmaceutical composition of the present invention to dysfunctional T cells.

In another aspect, the present invention provides a method for the treatment or prevention of cancer, comprising administering a therapeutically effective amount of the antibody, polynucleotide, polynucleotide combination, expression vector, conjugate and/or pharmaceutical composition of the present invention to a subject in need thereof.

In yet another aspect, the present invention provides use of the anti-PD-L1 antibody or antigen-binding fragment thereof, the polynucleotide, the polynucleotide combination, the corresponding nucleic acid construct or vector encoding the antibody or antigen-binding fragment thereof, the antibody-drug conjugate or the pharmaceutical composition of the present invention for the manufacture of a medicament for use in the treatment or prevention of cancer.

In yet another aspect, the present invention provides the antibody, polynucleotide, polynucleotide combination, expression vector, conjugate and/or pharmaceutical composition of the present invention, for use in the treatment or prevention of cancer.

Further, the cancer is a solid tumor.

Further, the solid tumor is lung cancer, colorectal cancer, breast cancer, ovarian cancer, melanoma, bladder cancer, urothelial cancer, kidney cancer, liver cancer, salivary cancer, stomach cancer, gliomas, thyroid cancer, thymic cancer, epithelial cancer, head and neck cancer, gastric and pancreatic cancer.

Further, the lung cancer is non-small cell lung cancer.

Further, the ovarian cancer is triple negative breast cancer.

Yet another aspect of the present invention provides a method for the treatment of T cell dysfunction, comprising administering a therapeutically effective amount of the above-mentioned pharmaceutical composition of the present invention to a patient with T cell dysfunction. The T cell dysfunction comprises infection and tumor immunization. The tumor immunization is caused by a cancer selected from breast cancer, lung cancer, colon cancer, ovarian cancer, melanoma, bladder cancer, kidney cancer, liver cancer, salivary cancer, stomach cancer, glioma, thyroid cancer, thymic cancer, epithelial cancer, head and neck cancer, and gastric and pancreatic cancer.

The present invention further provides use of the anti-PD-L1 antibody or antigen-binding fragment thereof, the polynucleotide, the polynucleotide combination, the corresponding nucleic acid construct or vector encoding the antibody or antigen-binding fragment thereof, the antibody-drug conjugate or the pharmaceutical composition of the present invention for the manufacture of a medicament for use in treatment or prevention of cancer.

The anti-PD-L1 monoclonal antibody provided by the present invention is a novel monoclonal antibody targeting PD-L1 with a new CDR sequence and amino acid sequence. The anti-PD-L1 monoclonal antibody provided by the present invention has a surprising affinity and specificity to human PD-L1, and has significant advantages in competing with human PD-1 to bind to human PD-L1. The anti-PD-L1 monoclonal antibody provided by the present invention exhibits unexpected tumor inhibitory effects in in vitro animal models of both non-small cell lung cancer and colorectal cancer, and provides a better option for inhibiting tumor progression.

DETAILED DESCRIPTION

Definitions

Unless defined otherwise, all technical and scientific terms used herein have the same meaning as understood by those ordinarily skilled in the art. With regard to the definitions and terms in the art, reference may be made to Current Protocols in Molecular Biology (Ausubel). The standard three- and/or one-letter code used for expressing one of 20 common L-amino acids in the art is adopted as the abbreviation of an amino acid residue.

In the present invention, a method for determining or numbering the complementarity determining region (CDR) of an antibody's variable domain includes IMGT, Kabat, Chothia, AbM and Contact, which are well known in the art.

For the purposes of the present invention, the "consistency", "identity" or "similarity" between two nucleic acid or amino acid sequences refers to the percentage of identical nucleotides or identical amino acid residues between the two sequences to be compared after optimal alignment. The percentage is purely statistical and the differences between the two sequences are randomly distributed and cover their full length. Sequence comparison between two nucleic acid or amino acid sequences are usually performed by comparing these sequences after they have been optimally matched, and the comparison can be performed on a segment or on a "comparison window". In addition to manual implementation, the optimal alignment for comparing sequences can also be performed by the local homology algorithm of Smith and Waterman (1981) [Ad. App. Math. 2: 482], the local homology algorithm of Neddleman and Wunsch (1970) [J. Mol. Biol. 48: 443], the similarity search method of Pearson and Lipman (1988) [Proc. Natl. Acad. Sci. USA 85: 2444), or a computer software using these algorithms (GAP, BEST-FIT, FASTA and TFASTA in the Wisconsin Genetics Software Package, Genetics Computer Group, 575Science Dr., Madison, WI, or BLAST N or BLAST P comparison software).

As used herein, "antibody" is used in a broadest sense and encompasses various antibodies including, but not limited to, a monoclonal antibody, a polyclonal antibody, and a multispecific antibody (e.g., a bispecific antibody). As used herein, "antigen-binding fragment" refers to an antibody fragment consisting of or comprising a partial sequence of a heavy or light variable chain of an antibody from which it is derived, wherein the partial sequence is capable of retaining the same binding specificity as the antibody from which it is derived and a sufficient affinity, preferably equal to at least $\frac{1}{100}$, more preferably at least $\frac{1}{10}$ of the affinity of the antibody from which it is derived. Such a functional fragment comprises a minimum of 5 amino acids, preferably 10, 15, 25, 50 or 100 contiguous amino acids of the antibody sequence from which it is derived, including (particularly) Fab, F(ab'), F(ab')$_2$, Fv, dAb, Fd, a complementarity determining region (CDR) fragment, a single chain antibody (scFv), and a bivalent single chain antibody, that contains at least an immunoglobulin fragment enough to allow a specific antigen to bind to the polypeptide. The above fragments can be prepared by a synthetic or enzymatic method, or by chemical cleavage of an intact immunoglobulin, or can be genetically engineered by recombinant DNA technology. The preparation methods thereof are well known in the art. A heavy chain contains a heavy chain variable region (abbreviated as VH) and a heavy chain constant region. The heavy chain constant region contains three domains, CH1, CH2 and CH3. A light chain contains a light chain variable region (abbreviated as VL) and a light chain constant region. The light chain constant region contains a domain, CL. VH and VL regions can be further subdivided into multiple regions with high variability, called as complementarity determining regions (CDRs), interspersed with more conservative regions called as framework regions (FRs). Each VH and VL is composed of three CDRs and four FRs, which are arranged from the amino terminal to the carboxy terminal in the following order: FR1, CDR1, FR2, CDR2, FR3, CDR3, FR4. These variable regions of the heavy and light chains contain a binding domain that interacts with an antigen. The constant region of an antibody can mediate binding of an immunoglobulin to a host tissue or factor, including various cells in the immune system (such as effector cells) and the first component of the classical complement system (Clq). Chimeric or humanized antibodies are also encompassed by the antibodies according to the present invention.

The term "humanized antibody" refers to an antibody that contains a CDR region derived from a non-human antibody, with the rest deriving from one (or several) human antibody. Moreover, in order to retain binding affinity, some residues at the backbone (called FR) segment can be modified (Jones et al., Nature, 321: 522-525, 1986; Verhoeyen et al., Science, 239: 1534-1536, 1988; Riechmann et al., Nature, 332: 323-327, 1988). Humanized antibodies or fragments thereof according to the present invention can be prepared by techniques known to those skilled in the art (e.g., described in the document Singer et al., J. Immun. 150: 2844-2857, 1992; Mountain et al., Biotechnol. Genet. Eng. Rev., 10: 1-142, 1992; or Bebbington et al., Bio/Technology, 10: 169-175, 1992).

The term "chimeric antibody" refers to an antibody in which the variable region sequence is from one species while the constant region sequence is from another species, for example, an antibody in which the variable region sequence is from a mouse antibody while the constant region sequence is from a human antibody. A chimeric antibody or a fragment thereof according to the present invention can be prepared by using genetic recombination technology. For example, the chimeric antibody can be produced by cloning a recombinant DNA comprising a promoter and a sequence encoding a variable region of a non-human, especially a murine monoclonal antibody according to the present invention, and a sequence encoding a constant region of a human antibody. The chimeric antibody of the present invention encoded by such a recombinant gene will be, for example, a murine-human chimera whose specificity is determined by the variable region derived from murine DNA, and the isotype is determined by the constant region derived from human DNA. For methods for preparing a chimeric antibody, for example, reference can be made to the document Verhoeyn et al. (BioEssays, 8:74, 1988).

The term "monoclonal antibody" refers to a preparation of an antibody molecule consisting of a single molecule. Monoclonal antibody compositions display a single binding specificity and affinity for a particular epitope.

The term an "isolated" nucleic acid molecule refers to a nucleic acid molecule identified and separated from at least one contaminant nucleic acid molecules, and is generally associated with the contaminant nucleic acid molecule in the natural source of an antibody nucleic acid. An isolated nucleic acid molecule is different in form or environment from when it is found in nature, and therefore different from that existing in natural cells. However, an isolated nucleic acid molecule comprises a nucleic acid molecule contained in cells where an antibody is usually expressed, and where for example, it is located on a different chromosomal position from that in a natural cell.

Generally, in order to prepare a monoclonal antibody or functional fragment thereof, especially a murine-derived monoclonal antibody or functional fragment thereof, reference can be made to the technology especially described in the manual "Antibodies" (Harlow and Lane, Antibodies: A Laboratory Manual, Cold Spring Harbor Laboratory, Cold Spring Harbor NY, pp. 726, 1988) or the technique for preparation from hybridoma cells described by Kohler and Milstein (Nature, 256: 495-497, 1975).

EXAMPLES

The embodiments of the present invention will be described in detail below in conjunction with examples. However, it will be understood by those skilled in the art that the following examples are only used to illustrate the present invention and should not be regarded as limiting the scope of the present invention.

Example 1 Production of Anti-PD-L1 Antibody

Through extensive screening of anti-PD-L1 antibodies obtained after immunizing mice, a candidate murine antibody mAAG5D8 was determined. After sequence alignment in the antibody variable region database, a human IgG1 framework region with a high homology to the murine PD-L1 antibody mAAG5D8 was determined. For mAAG5D8, a variety of humanized antibodies was further designed and compared for their affinity, and finally a candidate humanized anti-PD-L1 antibody hAAG5D8 was determined.

TABLE 6

CDRs 1-3 amino acid sequences of heavy chain and light chain variable regions of anti-PD-L1 humanized antibody hAAG5D8 (determined by IMGT method)

| Heavy chain | CDR1 | SEQ ID NO: 1 | GFSLSRYS |
|---|---|---|---|
| | CDR2 | SEQ ID NO: 2 | IWGVGTT |
| | CDR3 | SEQ ID NO: 3 | ARNWGTADYFDY |
| Light chain | CDR1 | SEQ ID NO: 4 | KSVHTSGYSY |
| | CDR2 | SEQ ID NO: 5 | LAS |
| | CDR3 | SEQ ID NO: 6 | QHSGELPYT |

The heavy chain variable region of anti-PD-L1 humanized antibody hAAG5D8 comprises an amino acid sequence of (SEQ ID NO: 31):

QVQLQESGPG LVKPSETLSL TCTVSGESLS RYSVHWIRQP PGKGLEWLGM IWGVGITDYN    60
SALKSRLTIS KDTSKNQFSL KLSSVTAADT AVYYCARNWG TADYFDYWGQ GTIVTVSSAS   120

The light chain variable region of anti-PD-L1 humanized antibody hAAG5D8 comprises an amino acid sequence of (SEQ ID NO: 32):

DIVLTQSPAS LAVSPGQRAT ITCRLSKEVH TSGYSIMHWY QQKPGQPPKI LIYLASNLES    60
GVPARFSGSG SGTDFTLTIN PVEANDTANY YCQHSGELPY TFGGGTKVEI KRT           113

The amino acid sequences of the heavy chain and light chain of anti-PD-L1 humanized antibody hAAG5D8 are shown in SEQ ID NO: 33 and SEQ ID NO: 34, respectively.

Example 2 Comparison of Affinity of hAAG5D8 to Human PD-L1

The affinity of hAAG5D8 to human PD-L1 was detected using biolayer interferometry (BLI). The wells in A-D columns 1, 3, and 5 of a black 96-well plate were added with a PBS solution as baseline 1, baseline 2 and a dissociation solution, respectively. The wells in column 2 were added with a PD-L1 solution (R&D company), in column 4 with a hAAG5D8 solution (The concentrations were as follows: 100 nM, 50 nM, 25 nM, and 0 nM), in column 10 with an imidazole solution, in column 11 with water, and in column 12 with a nickel sulfate solution. Ni-NTA probe (Fortebio) was employed in the experiment. First, the probe was dipped in A-D column 1 for 180 seconds to stabilize the baseline. The Ni-NTA probe was then dipped in A-D column 2 for 300 seconds to immobilize PD-L1 on the probe. The Ni-NTA probe was then dipped in A-D column 3 for 120 seconds to stabilize the baseline. The Ni-NTA probe was then dipped in A-D column 4 for 600 seconds to allow the binding of hAAG5D8 with a different concentration to the immobilized PD-L1 protein on the probe. The Ni-NTA probe was then dipped in A-D column 5 for 600 seconds to allow the antibody to dissociate spontaneously. Finally, the Ni-NTA probe was dipped in A-D columns 10, 11, and 12 successively to force the immobilized PD-L1 dissociating from the probe. Data analysis was performed by Data analysis 7.0 to obtain the binding and dissociation equilibrium constant $K_D$.

Figure 1:
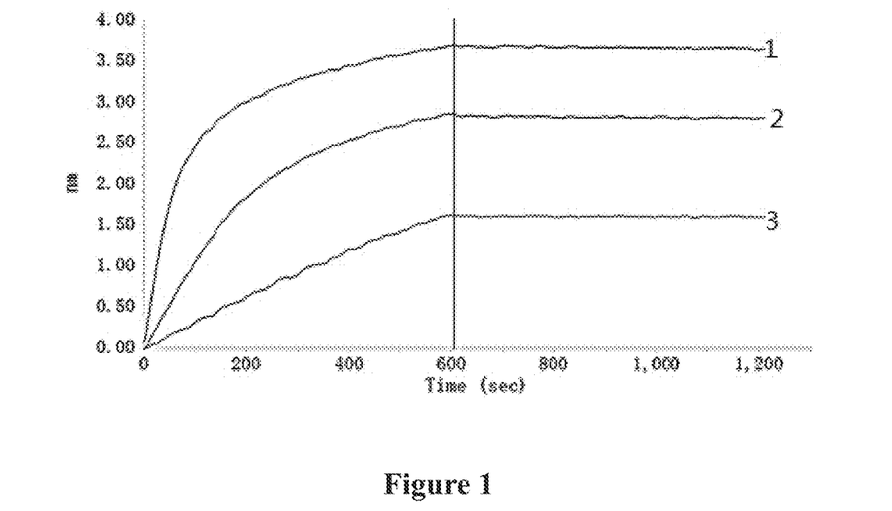
FIG. 1 shows an affinity binding and dissociation curve of hAAG5D8 to human PD-L1, where the curve 1 indicates 100 nM hAAG5D8, the curve 2 indicates 50 nM hAAG5D8, and the curve 3 indicates 25 nM hAAG5D8.

Results and conclusions: The binding and dissociation equilibrium constant $K_D$ value and affinity binding and dissociation curve of hAAG5D8 to human PD-L1 are shown in Table 7 and FIG. 1, respectively. The experimental results show that the affinity of hAAG5D8 to human PD-L1 is much higher than the affinity of PD-1 to PD-L1 of 8.2 M (Molecular Interactions of Antibody Drugs Targeting PD-1, PD-L1, and CTLA-4 in Immuno-Oncology, Hyun Tae Lee et al., Molecules 2019, 24, 1190; doi:10.3390/molecules24061190, Mar. 26, 2019, last paragraph on page 4).

TABLE 7

| Affinity kinetic constant of anti-PD-L1 antibody binding to PD-L1 | |
|---|---|
| Main parameter | $K_D(M)$ |
| Affinity kinetic constant | 7.62E−11 ± 3.32E−11 |

Example 3 Competing Between hAAG5D8 and Human PD-1 for Binding

The ability of hAAG5D8 to compete with PD-1 to bind to PD-L1 was tested by ELISA. PD-L1 (Fc Tag) was diluted to 1 µg/mL with a coating buffer (6 mM $Na_2CO_3$, 14 mM $NaHCO_3$), and then added 100 µL to each well followed by overnight incubation at 4° C. The plate was then washed with PBST, and added with 250 µL of a blocking solution (3% BSA/PBST) to each well to block for 2 h at 25° C. Afterwards, the plate was washed with PBST and added with 50 µL of human PD-1 at a concentration of 6 µg/mL as well as 50 µL of a gradiently diluted hAAG5D8 solution (at a concentration of 8000 ng/mL, 2000 ng/mL, 500 ng/mL, 250 ng/mL, 125 ng/mL, 62.5 ng/mL, 31.25 ng/mL, 6.25 ng/mL, or 1.25 ng/mL) to each well followed by mixing well and incubation at 25° C. for 2 h. Next, the plate was washed with PBST and added with 100 μL of an enzyme-labeled secondary antibody (goat anti-human IgG-Fc-HRP diluted 1:5000) to each well, followed by incubation at 25° C. for 1 h. Finally, color development was performed and values were read at 450 nm. A four-parameter equation was used for curve fitting to calculate the $EC_{50}$ value.

Figure 2:
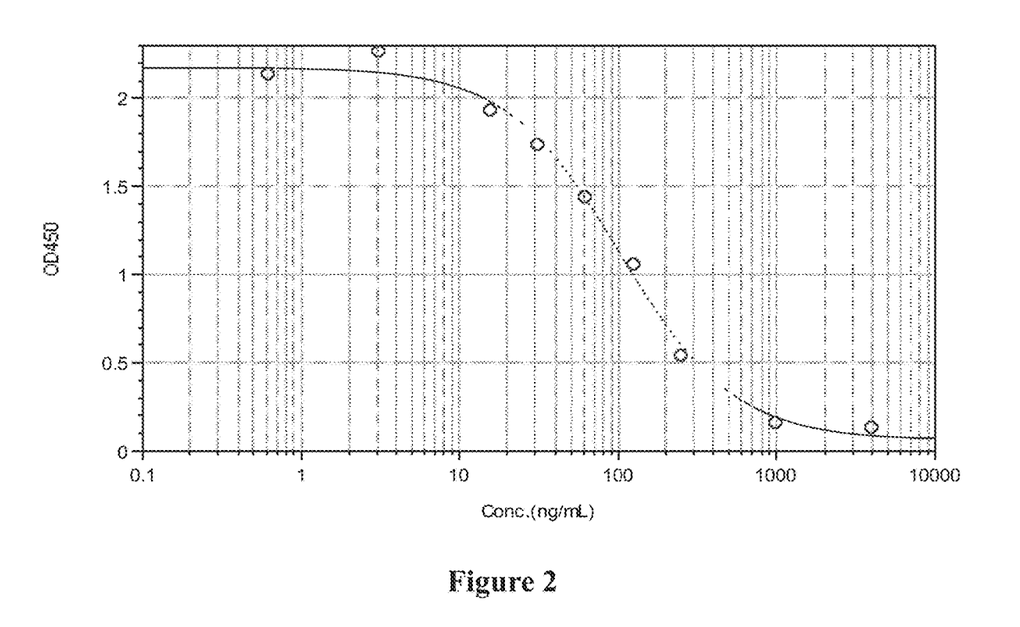
FIG. 2 shows a curve of competing between hAAG5D8 and human PD-1 for binding.

Results and conclusions: $EC_{50}$ value and the competitive binding curve of hAAG5D8 competitively binding to human PD-L1 are shown in Table 8 and FIG. 2, respectively. Experimental results show that hAAG5D8 can effectively block the binding of PD-1 to PD-L1.

TABLE 8

| Competing between hAAG5D8 and human PD-1 for binding (pM, Mean ± SD) | |
|---|---|
| Main parameter | Anti-PD-L1 antibody |
| $EC_{50}$ of competing with human PD-1 | 715.56 ± 61.58 |

Example 4 Affinity of hAAG5D8 to a Variety of Other B7 Family Proteins

The affinity of hAAG5D8 to a variety of other B7 family proteins (PD-L1, PD-L2, B7-H3, PD-1 and CD80) was tested by ELISA. hAAG5D8 was diluted to 100 μg/mL with a coating buffer (6 mM $Na_2CO_3$, 14 mM $NaHCO_3$), and then added 100 μL to each well followed by overnight incubation at 4° C. The plate was then washed with PBST, and added with 250 μL of a blocking solution (3% BSA/PBST) to each well to block for 2 h at 25° C. Afterwards, the plate was washed with PBST and added with 100 μL of a protein sample (rhPD-L1, rhPD-L2, rhB7-H3, rhPD-1 or rhCD80) at a concentration of 5 μg/mL to each well followed by incubation at 25° C. for 2 h. Next, the plate was washed with PBST and added with 100 μL of an enzyme-labeled secondary antibody (the secondary antibody anti-His-tag diluted 1:5000) to each well followed by incubation at 25° C. for 1 h. Finally, the plate was washed with PBST and then color development is performed. Values were read at 450 nm.

Figure 3:
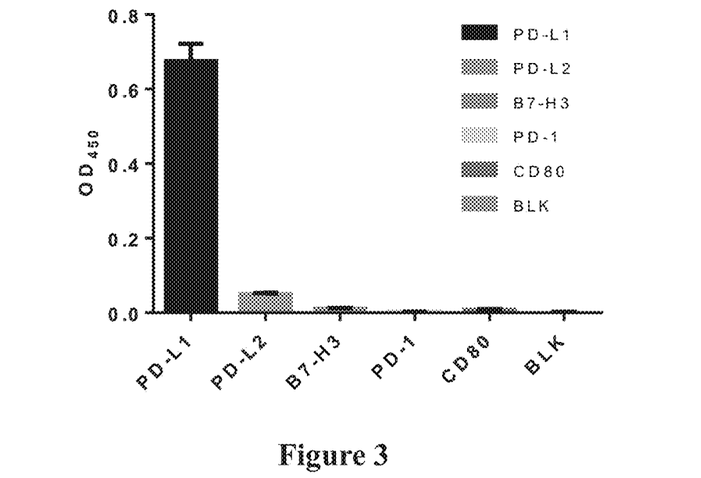
FIG. 3 shows the binding ability of hAAG5D8 to various B7 family proteins (PD-L1, PD-L2, B7-H3, PD-1 and CD80).

Results and conclusions: The binding of hAAG5D8 to a B7 family protein (PD-L1, PD-L2, B7-H3, PD-1 or CD80) is shown in FIG. 3. The results show that hAAG5D8 can specifically bind to PD-L1 but not PD-L2, and hAAG5D8 does not bind to other proteins of the same family with related functions (B7-H3, PD-1, and CD80). Accordingly, hAAG5D8 binds to PD-L1 with extremely high specificity.

Example 5 Study on the Therapeutic Efficacy of hAAG5D8 on Subcutaneously Transplanted Tumor in Human Non-Small Cell Lung Cancer HCC827 NCG Mice Twelve highly immunodeficient male NCG mice aged 4-5 weeks, weighing 20-26 g (purchased from Model Animal Research Center of Nanjing University) were injected with 100 μl of human peripheral blood mononuclear cells PBMC ($1 \times 10^7$ cells/100 μl, isolated from blood of healthy donors) via tail vein injection. Three days after tail vein injection, mice were inoculated subcutaneously with human non-small cell lung cancer HCC827 cells (ATCC) on the right flank. Three days after inoculation (an average tumor volume of 57 $mm^3$), the mice were randomly divided into 3 groups (A-1 group, A-2 group, and A-3 group) with 4 mice in each group, and administered according to the dosage regimen shown in Table 9. Both positive control and negative control were set in this experiment, wherein the positive control was MPDL3820A (i.e. Atezolizumab) and the negative control was Human IgG1 (Crown Bioscience (Taicang) Co., Ltd., lot no. AB160083). On the day of the fourth administration (that is, the 13th day after inoculation of tumor cells), the experimental mice were euthanized under $CO_2$ and then tumors were taken. The relative tumor inhibition ($TGI_{RTV}$) and the tumor growth inhibition ($TGI_{ATV}$) were calculated for evaluation of drug efficacy.

The equation for calculating the relative tumor inhibition: $TGI_{RTV}=1-T_{RTV}/C_{RTV}$ (%). ($T_{RTV}$ is the relative tumor volume (TV) of the positive control group or treatment group at a specific time point, $C_{RTV}$ is the relative tumor volume of the negative control group at a specific time point, $T_{RTV}/C_{RTV}$ is the percentage value of the relative tumor volume of the positive control group or treatment group and the relative tumor volume of the negative control group, $RTV=V_t/V_0$, $V_0$ is the tumor volume of the animal at the time of grouping, and $V_t$ is the tumor volume of the animal after treatment.)

The equation for calculating the tumor growth inhibition: $TGI_{ATV}\%=(1-\Delta T/\Delta C)\times 100\%$. ($\Delta T$=the average tumor volume of the positive control group or treatment group at a specific time point–the average tumor volume of the positive control group or the treatment group at the beginning of administration, and $\Delta C$=the average tumor volume of the negative control group at a specific time point–the average tumor volume of the negative control group at the beginning of administration.)

Figure 4:
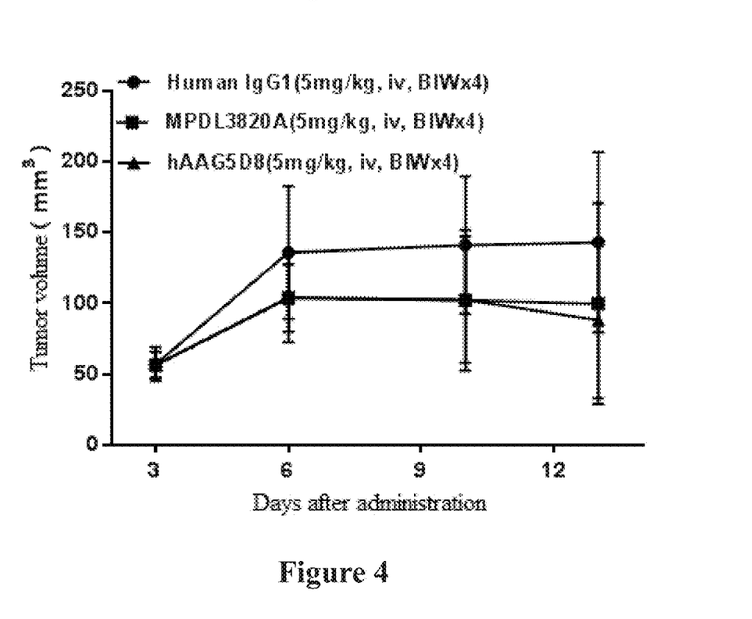
FIG. 4 shows the growth curve of tumor after administration of hAAG5D8 (5 mg/kg), MPDL3820A (5 mg/kg, positive control) or human IgG1 (5 mg/kg, negative control) in a subcutaneous xenograft tumor model of human non-small cell lung cancer.

Results and conclusions: The tumor inhibitory effects of hAAG5D8 on human non-small cell lung cancer models are shown in Table 10 and FIG. 4, respectively. Table 10 shows the relative tumor inhibition and tumor growth inhibition of hAAG5D8 on human non-small cell lung cancer cells, and FIG. 4 shows tumor growth curves after administration. Experimental results show that hAAG5D8 has a significant inhibitory effect on human non-small cell lung cancer.

TABLE 9

Dosage regimen for studying the tumor inhibitory activity of hAAG5D8 on human non-small cell lung cancer

| Group | Subject | Drug | Dose (mg/kg) | Route | Volume | Period |
|---|---|---|---|---|---|---|
| 1 | A-1 group | Human IgG1 | 5 | Intravenous injection | 10 μL/g | BIW × 4 times |
| 2 | A-2 group | MPDL3820A | 5 | Intravenous injection | 10 μL/g | BIW × 4 times |
| 3 | A-3 group | hAAG5D8 | 5 | Intravenous injection | 10 μL/g | BIW × 4 times |

Note:
Group 1 is the negative control group, Group 2 is the positive control group, and Group 3 is the treatment group.

TABLE 10

Relative tumor inhibition rand tumor growth inhibition of hAAG5D8 on human non-small cell lung cancer tumor cells

| Drug | $TGI_{RTV}(\%)$ | $TGI_{\Delta TV}(\%)$ |
|---|---|---|
| Human IgG1 (5 mg/kg), | — | — |
| MPDL3820A (5 mg/kg) | 25.3 | 49.5 |
| hAAG5D8 (5 mg/kg) | 35.9 | 63.3 |

Figure 5:
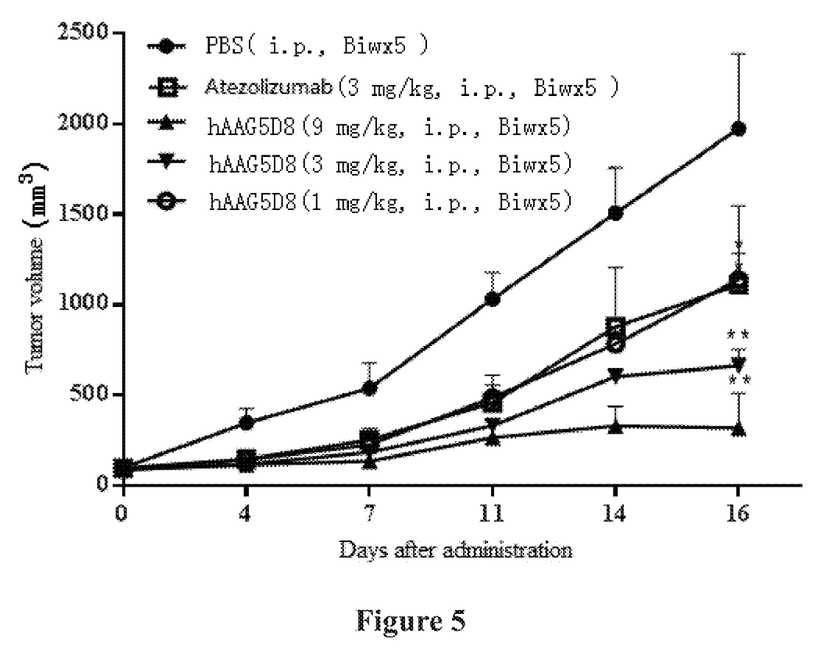
FIG. 5 shows the change in tumor volume after administration of hAAG5D8 (1 mg/kg, 3 mg/kg, or 9 mg/kg), MPDL3820A (10 mg/kg, positive control) or PBS (negative control) in a subcutaneous xenograft tumor model of human colorectal cancer.

Example 6 Study on the Therapeutic Efficacy of hAAG5D8 on Subcutaneously Transplanted Tumor in Mouse Colorectal Cancer MC38 Transgenic Mice Each of 30 human PD-1 transgenic female C57 mice (Animal Experiment Center of Tongji University) was implanted subcutaneously $3 \times 10^6$ mouse colorectal cancer cells expressing human PD-L1 (Tongji University, code: MC38-hPD-L1) on the left flank. When the tumor volume reached about 100 mm³, the mice were randomly divided into 5 groups: C-1 group (negative control group, PBS, 6 mice), C-2 group (positive control group, Atezolizumab, 3 mg/kg, 6 mice), C-3 group (administration group, hAAG5D8, 1 mg/kg, 6 mice), C-4 group (administration group, hAAG5D8, 3 mg/kg, 6 mice) and C-5 group (administration group, hAAG5D8, 9 mg/kg, 6 mice). The mice were administered intraperitoneally 2 times a week, 5 times in total. The tumor volume was measured twice a week until the 16th day after the beginning of administration.
Calculation Equations:
Tumor volume: $TV = D1 \times D2^2/2$, wherein D1 and D2 represent tumor long diameter and tumor short diameter, respectively.
Relative tumor volume: $RTV = T_{VT}/T_{V1}$, where $T_{V1}$ is the tumor volume before administration, and $T_{VT}$ is the tumor volume on each measurement.
Relative tumor proliferation: $T/C(\%) = T_{RT}V/C_{RT}V \times 100\%$, wherein $T_{RT}V$ represents the RTV of the treatment group or positive control group, and $C_{RT}V$ represents the RTV of the negative control group.
Relative tumor inhibition: $TGI_{RTV}(\%) = (1 - T_{RTV}/C_{RTV}) \times 100\%$.
Results and conclusions: The tumor inhibitory effects of hAAG5D8 on mouse colorectal cancer are shown in Table 11 and FIG. 5. The results show that hAAG5D8 at a concentration of 3 mg/kg or above has a significant tumor inhibitory effect on subcutaneously transplanted tumors of mouse colorectal cancer. At the dose of 3 mg/kg, the tumor inhibitory effect of the anti-PD-L1 antibody has been significantly superior to that of Atezolizumab.

TABLE 11

Tumor volume changes in tumor-bearing mice after administration

| Group | Dose (mg/kg) | Tumor volume TV (mm³) D0 | Tumor volume TV (mm³) D16 | $T_{RTV}/C_{RTV}(\%)$ | $TGI_{RTV}$ (%) |
|---|---|---|---|---|---|
| PBS | — | 99.9 ± 13.2 | 1974.2 ± 413.2 | — | — |
| Atezolizumab | 3 | 95.9 ± 16.8 | 1111.6 ± 435.2* | 53 | 47 |
| hAAG5D8 | 1 | 95.5 ± 9.8 | 1138.8 ± 144.9* | 64 | 36 |
| hAAG5D8 | 3 | 90.7 ± 12.4 | 664.8 ± 92.0** | 39 | 61 |
| hAAG5D8 | 9 | 91.2 ± 15.9 | 319.1 ± 0190.4** | 14 | 86 |

Note: The day of administration was defined as D0; *P < 0.05, **P < 0.01 vs PBS

REFERENCES

1. CHEN L, FLIES D B. Molecular mechanisms of T cell co-stimulation and co-inhibition [J]. Nature reviews Immunology, 2013, 13(4): 227-42.
2. OHAEGBULAM K C, ASSALA, LAZAR-MOLNAR E, et al. Human cancer immunotherapy with antibodies to the PD-1 and PD-L1 pathway [J]. Trends in molecular medicine, 2015, 21(1): 24-33.
3. ISHIDA M, IWAI Y, TANAKA Y, et al. Differential expression of PD-L1 and PD-L2, ligands for an inhibitory receptor PD-1, in the cells of lymphohematopoietic tissues [J]. Immunology letters, 2002, 84(1): 57-62.
4. TAUBE J M, ANDERS R A, YOUNG G D, et al. Colocalization of inflammatory response with B7-h1 expression in human melanocytic lesions supports an adaptive resistance mechanism of immune escape [J]. Science translational medicine, 2012, 4(127): 127ra37.
5. TSENG S Y, OTSUJI M, GORSKI K, et al. B7-DC, a new dendritic cell molecule with potent costimulatory properties for T cells [J]. The Journal of experimental medicine, 2001, 193(7): 839-46.
6. BUTTE M J, KEIR M E, PHAMDUY T B, et al. Programmed death-1 ligand 1 interacts specifically with the B7-1 costimulatory molecule to inhibit T cell responses [J]. Immunity, 2007, 27(1): 111-22.
7. CHENG X, VEVERKA V, RADHAKRISHNAN A, et al. Structure and interactions of the human programmed cell death 1 receptor [J]. The Journal of biological chemistry, 2013, 288(17): 11771-85.
8. An Liu, Discovery on small molecular inhibitors of PD-1/PD-L1 pathway [D], Jilin: Jilin University School of Pharmaceutical Sciences, 2016, 15.

The invention claimed is:

1. An isolated anti-PD-L1 antibody or antigen-binding fragment thereof comprising a heavy chain variable region and a light chain variable region, wherein the heavy chain variable region and the light chain variable region comprise the following CDRs:
   (1) CDRs 1-3 of the heavy chain variable region comprising the amino acid sequences of SEQ ID NOs: 1-3 respectively, and the CDRs 1-3 of the light chain variable region comprising the amino acid sequences of SEQ ID NOs: 4-6 respectively; or
   (2) CDRs 1-3 of the heavy chain variable region comprising the amino acid sequences of SEQ ID NOs: 7-9 respectively, and CDRs 1-3 of the light chain variable region comprising the amino acid sequences of SEQ ID NOs: 10-12 respectively; or
   (3) CDRs 1-3 of the heavy chain variable region comprising the amino acid sequences of SEQ ID NOs: 13-15 respectively, and CDRs 1-3 of the light chain variable region comprising the amino acid sequences of SEQ ID NOs: 16-18 respectively; or
   (4) CDRs 1-3 of the heavy chain variable region comprising the amino acid sequences of SEQ ID NOs: 19-21 respectively, and CDRs 1-3 of the light chain variable region comprising the amino acid sequences of SEQ ID NOs: 22-24 respectively; or
   (5) CDRs 1-3 of the heavy chain variable region comprising the amino acid sequences of SEQ ID NOs: 25-27 respectively, and CDRs 1-3 of the light chain variable region comprising the amino acid sequences of SEQ ID NOs: 28-30 respectively.

2. The antibody or antigen-binding fragment thereof according to claim 1, wherein:
   (1) the heavy chain variable region comprises the same CDRs 1-3 as in SEQ ID NO: 31 and are more than 95% identical to SEQ ID NO: 31; and
   (2) the light chain variable region comprises the same CDRs 1-3 as in SEQ ID NO: 32 and are more than 95% identical to SEQ ID NO: 32.

3. The antibody or antigen-binding fragment thereof according to claim 1, wherein:
   (1) the heavy chain variable region comprises the amino acid sequence as shown in SEQ ID NO: 31; and
   (2) the light chain variable region comprises the amino acid sequence as shown in SEQ ID NO: 32.

4. The antibody or antigen-binding fragment thereof according to claim 1, wherein the antibody is a monoclonal antibody, chimeric antibody, humanized antibody, bispecific antibody, multispecific antibody or Fab Fragment, F(ab') fragment, F(ab')$_2$ fragment, Fv fragment, dAb, Fd, or single chain antibody (scFv).

5. An isolated polynucleotide encoding the antibody or antigen-binding fragment thereof according to claim 1.

6. A combination of an isolated polynucleotide encoding the heavy chain of the antibody or antigen-binding fragment thereof according to claim 1 and an isolated polynucleotide encoding the light chain of the antibody or antigen-binding fragment thereof according to claim 1.

7. A nucleic acid construct comprising the polynucleotide according to claim 5.

8. A host cell comprising the nucleic acid construct of claim 7.

9. An antibody-drug conjugate comprising the antibody or antigen-binding fragment thereof according to claim 1 and a drug toxin.

10. A composition comprising the antibody or antigen-binding fragment thereof according to claim 1, and a pharmaceutically acceptable carrier.

11. A method for the manufacture of an anti-PD-L1 antibody, comprising culturing the host cell according to claim 8 under a condition suitable for a vector encoding the anti-PD-L1 antibody or antigen-binding fragment to be expressed, and recovering the antibody or fragment.

12. The antibody or antigen-binding fragment thereof according to claim 1, wherein:
 (1) the heavy chain comprises the amino acid sequence as shown in SEQ ID NO: 33; and
 (2) the light chain comprises the amino acid sequence as shown in SEQ ID NO: 34.

* * * * *

UNITED STATES PATENT AND TRADEMARK OFFICE
CERTIFICATE OF CORRECTION

Page 1 of 1

PATENT NO. : 12,404,333 B2
APPLICATION NO. : 17/312884
DATED : September 2, 2025
INVENTOR(S) : Jianmin Fang et al.

It is certified that error appears in the above-identified patent and that said Letters Patent is hereby corrected as shown below:

In the Specification

Column 1, Line 46-50, delete
"immunotherapy.
    Among the known immune checkpoints, PD-1/PD-L1 has drawn high attention in tumor immune the anti-PD-L1 antibody or antigen-binding fragment to be expressed, and recovering the antibody or fragment." and insert
-- immunotherapy. Among the known immune checkpoints, PD-1/PD-L1 has drawn high attention in tumor immune research and therapy. --.

Column 3, Line 33 (approx.), delete "of Neddleman and" and insert -- of Needleman and --.

Column 3, Line 38 (approx.), delete "Group, 575Science Dr.," and insert -- Group, 575 Science Dr., --.

Column 5-6, Line 47 (approx.), delete "TCTVSGESLS" and insert -- TCTVSGFSLS --.

Column 5-6, Line 52 (approx.), delete "LAVSPGQRAT ITCRLSKEVH TSGYSIMHWY QQKPGQPPKI" and insert -- LAVSPGQRAT ITCRASKSVH TSGYSYMHWY QQKPGQPPKL --.

Column 6, Line no. 28 (approx.), delete "8.2 M (Molecular" and insert -- 8.2 µM (Molecular --.

Column 8, Line no. 39 (approx.), delete "and AC=the" and insert -- and ΔC=the --.

Signed and Sealed this
Eighteenth Day of November, 2025

John A. Squires
*Director of the United States Patent and Trademark Office*

SEQUENCE LISTING

<160> NUMBER OF SEQ ID NOS: 34

<210> SEQ ID NO 1
<211> LENGTH: 8
<212> TYPE: PRT
<213> ORGANISM: Artificial sequence
<220> FEATURE:
<223> OTHER INFORMATION: peptide

<400> SEQUENCE: 1

Gly Phe Ser Leu Ser Arg Tyr Ser
1               5

<210> SEQ ID NO 2
<211> LENGTH: 7
<212> TYPE: PRT

<213> ORGANISM: Artificial sequence
<220> FEATURE:
<223> OTHER INFORMATION: peptide

<400> SEQUENCE: 2

```
Ile Trp Gly Val Gly Thr Thr
1               5
```

<210> SEQ ID NO 3
<211> LENGTH: 12
<212> TYPE: PRT
<213> ORGANISM: Artificial sequence
<220> FEATURE:
<223> OTHER INFORMATION: peptide

<400> SEQUENCE: 3

```
Ala Arg Asn Trp Gly Thr Ala Asp Tyr Phe Asp Tyr
1               5                   10
```

<210> SEQ ID NO 4
<211> LENGTH: 10
<212> TYPE: PRT
<213> ORGANISM: Artificial sequence
<220> FEATURE:
<223> OTHER INFORMATION: peptide

<400> SEQUENCE: 4

```
Lys Ser Val His Thr Ser Gly Tyr Ser Tyr
1               5                   10
```

<210> SEQ ID NO 5
<211> LENGTH: 3
<212> TYPE: PRT
<213> ORGANISM: Artificial sequence
<220> FEATURE:
<223> OTHER INFORMATION: peptide

<400> SEQUENCE: 5

```
Leu Ala Ser
1
```

<210> SEQ ID NO 6
<211> LENGTH: 9
<212> TYPE: PRT
<213> ORGANISM: Artificial sequence
<220> FEATURE:
<223> OTHER INFORMATION: peptide

<400> SEQUENCE: 6

```
Gln His Ser Gly Glu Leu Pro Tyr Thr
1               5
```

<210> SEQ ID NO 7
<211> LENGTH: 5
<212> TYPE: PRT
<213> ORGANISM: Artificial sequence
<220> FEATURE:
<223> OTHER INFORMATION: peptide

<400> SEQUENCE: 7

```
Arg Tyr Ser Val His
1               5
```

<210> SEQ ID NO 8
<211> LENGTH: 16
<212> TYPE: PRT
<213> ORGANISM: Artificial sequence

```
<220> FEATURE:
<223> OTHER INFORMATION: peptide

<400> SEQUENCE: 8

Met Ile Trp Gly Val Gly Thr Thr Asp Tyr Asn Ser Ala Leu Lys Ser
1               5                   10                  15

<210> SEQ ID NO 9
<211> LENGTH: 10
<212> TYPE: PRT
<213> ORGANISM: Artificial sequence
<220> FEATURE:
<223> OTHER INFORMATION: peptide

<400> SEQUENCE: 9

Asn Trp Gly Thr Ala Asp Tyr Phe Asp Tyr
1               5                   10

<210> SEQ ID NO 10
<211> LENGTH: 15
<212> TYPE: PRT
<213> ORGANISM: Artificial sequence
<220> FEATURE:
<223> OTHER INFORMATION: peptide

<400> SEQUENCE: 10

Arg Ala Ser Lys Ser Val His Thr Ser Gly Tyr Ser Tyr Met His
1               5                   10                  15

<210> SEQ ID NO 11
<211> LENGTH: 7
<212> TYPE: PRT
<213> ORGANISM: Artificial sequence
<220> FEATURE:
<223> OTHER INFORMATION: peptide

<400> SEQUENCE: 11

Leu Ala Ser Asn Leu Glu Ser
1               5

<210> SEQ ID NO 12
<211> LENGTH: 9
<212> TYPE: PRT
<213> ORGANISM: Artificial sequence
<220> FEATURE:
<223> OTHER INFORMATION: peptide

<400> SEQUENCE: 12

Gln His Ser Gly Glu Leu Pro Tyr Thr
1               5

<210> SEQ ID NO 13
<211> LENGTH: 7
<212> TYPE: PRT
<213> ORGANISM: Artificial sequence
<220> FEATURE:
<223> OTHER INFORMATION: peptide

<400> SEQUENCE: 13

Gly Phe Ser Leu Ser Arg Tyr
1               5

<210> SEQ ID NO 14
<211> LENGTH: 5
<212> TYPE: PRT
<213> ORGANISM: Artificial sequence
<220> FEATURE:
```

```
<223> OTHER INFORMATION: peptide

<400> SEQUENCE: 14

Trp Gly Val Gly Thr
1               5

<210> SEQ ID NO 15
<211> LENGTH: 10
<212> TYPE: PRT
<213> ORGANISM: Artificial sequence
<220> FEATURE:
<223> OTHER INFORMATION: peptide

<400> SEQUENCE: 15

Asn Trp Gly Thr Ala Asp Tyr Phe Asp Tyr
1               5                  10

<210> SEQ ID NO 16
<211> LENGTH: 15
<212> TYPE: PRT
<213> ORGANISM: Artificial sequence
<220> FEATURE:
<223> OTHER INFORMATION: peptide

<400> SEQUENCE: 16

Arg Ala Ser Lys Ser Val His Thr Ser Gly Tyr Ser Tyr Met His
1               5                  10                  15

<210> SEQ ID NO 17
<211> LENGTH: 7
<212> TYPE: PRT
<213> ORGANISM: Artificial sequence
<220> FEATURE:
<223> OTHER INFORMATION: peptide

<400> SEQUENCE: 17

Leu Ala Ser Asn Leu Glu Ser
1               5

<210> SEQ ID NO 18
<211> LENGTH: 9
<212> TYPE: PRT
<213> ORGANISM: Artificial sequence
<220> FEATURE:
<223> OTHER INFORMATION: peptide

<400> SEQUENCE: 18

Gln His Ser Gly Glu Leu Pro Tyr Thr
1               5

<210> SEQ ID NO 19
<211> LENGTH: 10
<212> TYPE: PRT
<213> ORGANISM: Artificial sequence
<220> FEATURE:
<223> OTHER INFORMATION: peptide

<400> SEQUENCE: 19

Gly Phe Ser Leu Ser Arg Tyr Ser Val His
1               5                  10

<210> SEQ ID NO 20
<211> LENGTH: 9
<212> TYPE: PRT
<213> ORGANISM: Artificial sequence
<220> FEATURE:
<223> OTHER INFORMATION: peptide
```

```
<400> SEQUENCE: 20

Met Ile Trp Gly Val Gly Thr Thr Asp
1               5

<210> SEQ ID NO 21
<211> LENGTH: 10
<212> TYPE: PRT
<213> ORGANISM: Artificial sequence
<220> FEATURE:
<223> OTHER INFORMATION: peptide

<400> SEQUENCE: 21

Asn Trp Gly Thr Ala Asp Tyr Phe Asp Tyr
1               5                   10

<210> SEQ ID NO 22
<211> LENGTH: 15
<212> TYPE: PRT
<213> ORGANISM: Artificial sequence
<220> FEATURE:
<223> OTHER INFORMATION: peptide

<400> SEQUENCE: 22

Arg Ala Ser Lys Ser Val His Thr Ser Gly Tyr Ser Tyr Met His
1               5                   10                  15

<210> SEQ ID NO 23
<211> LENGTH: 7
<212> TYPE: PRT
<213> ORGANISM: Artificial sequence
<220> FEATURE:
<223> OTHER INFORMATION: peptide

<400> SEQUENCE: 23

Leu Ala Ser Asn Leu Glu Ser
1               5

<210> SEQ ID NO 24
<211> LENGTH: 9
<212> TYPE: PRT
<213> ORGANISM: Artificial sequence
<220> FEATURE:
<223> OTHER INFORMATION: peptide

<400> SEQUENCE: 24

Gln His Ser Gly Glu Leu Pro Tyr Thr
1               5

<210> SEQ ID NO 25
<211> LENGTH: 6
<212> TYPE: PRT
<213> ORGANISM: Artificial sequence
<220> FEATURE:
<223> OTHER INFORMATION: peptide

<400> SEQUENCE: 25

Ser Arg Tyr Ser Val His
1               5

<210> SEQ ID NO 26
<211> LENGTH: 12
<212> TYPE: PRT
<213> ORGANISM: Artificial sequence
<220> FEATURE:
<223> OTHER INFORMATION: peptide
```

```
<400> SEQUENCE: 26

Trp Leu Gly Met Ile Trp Gly Val Gly Thr Thr Asp
1               5                   10

<210> SEQ ID NO 27
<211> LENGTH: 11
<212> TYPE: PRT
<213> ORGANISM: Artificial sequence
<220> FEATURE:
<223> OTHER INFORMATION: peptide

<400> SEQUENCE: 27

Ala Arg Asn Trp Gly Thr Ala Asp Tyr Phe Asp
1               5                   10

<210> SEQ ID NO 28
<211> LENGTH: 11
<212> TYPE: PRT
<213> ORGANISM: Artificial sequence
<220> FEATURE:
<223> OTHER INFORMATION: peptide

<400> SEQUENCE: 28

His Thr Ser Gly Tyr Ser Tyr Met His Trp Tyr
1               5                   10

<210> SEQ ID NO 29
<211> LENGTH: 10
<212> TYPE: PRT
<213> ORGANISM: Artificial sequence
<220> FEATURE:
<223> OTHER INFORMATION: peptide

<400> SEQUENCE: 29

Leu Leu Ile Tyr Leu Ala Ser Asn Leu Glu
1               5                   10

<210> SEQ ID NO 30
<211> LENGTH: 8
<212> TYPE: PRT
<213> ORGANISM: Artificial sequence
<220> FEATURE:
<223> OTHER INFORMATION: peptide

<400> SEQUENCE: 30

Gln His Ser Gly Glu Leu Pro Tyr
1               5

<210> SEQ ID NO 31
<211> LENGTH: 120
<212> TYPE: PRT
<213> ORGANISM: Artificial sequence
<220> FEATURE:
<223> OTHER INFORMATION: peptide

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Arg Tyr
            20                  25                  30

Ser Val His Trp Ile Arg Gln Pro Pro Gly Lys Gly Leu Glu Trp Leu
        35                  40                  45

Gly Met Ile Trp Gly Val Gly Thr Thr Asp Tyr Asn Ser Ala Leu Lys
    50                  55                  60
```

```
Ser Arg Leu Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Trp Gly Thr Ala Asp Tyr Phe Asp Tyr Trp Gly Gln Gly Thr
            100                 105                 110

Thr Val Thr Val Ser Ser Ala Ser
        115                 120

<210> SEQ ID NO 32
<211> LENGTH: 113
<212> TYPE: PRT
<213> ORGANISM: Artificial sequence
<220> FEATURE:
<223> OTHER INFORMATION: peptide

<400> SEQUENCE: 32

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Lys Ser Val His Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Ser Gly
                 85                  90                  95

Glu Leu Pro Tyr Thr Phe Gly Gly Gly Thr Lys Val Glu Ile Lys Arg
            100                 105                 110

Thr

<210> SEQ ID NO 33
<211> LENGTH: 450
<212> TYPE: PRT
<213> ORGANISM: Artificial sequence
<220> FEATURE:
<223> OTHER INFORMATION: peptide

<400> SEQUENCE: 33

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Arg Tyr
                20                  25                  30

Ser Val His Trp Ile Arg Gln Pro Pro Gly Lys Gly Leu Glu Trp Leu
            35                  40                  45

Gly Met Ile Trp Gly Val Gly Thr Thr Asp Tyr Asn Ser Ala Leu Lys
 50                  55                  60

Ser Arg Leu Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asn Trp Gly Thr Ala Asp Tyr Phe Asp Tyr Trp Gly Gln Gly Thr
            100                 105                 110

Thr Val Thr Val Ser Ser Ala Ser Ala Ser Thr Lys Gly Pro Ser Val
        115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 34
<211> LENGTH: 220
<212> TYPE: PRT
<213> ORGANISM: Artificial sequence
<220> FEATURE:
<223> OTHER INFORMATION: peptide

<400> SEQUENCE: 34

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val His Thr Ser
                20                  25                  30
```

-continued

```
Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65              70                  75                  80

Pro Val Glu Ala Asn Asp Thr Ala Asn Tyr Tyr Cys Gln His Ser Gly
                 85                  90                  95

Glu Leu Pro Tyr Thr Phe Gly Gly Gly Thr Lys Val Glu Ile Lys Arg
             100                 105                 110

Thr Arg Thr Val Ala Ala Pro Ser Val Phe Ile Phe Pro Pro Ser Asp
             115                 120                 125

Glu Gln Leu Lys Ser Gly Thr Ala Ser Val Val Cys Leu Leu Asn Asn
         130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                 165                 170                 175

Ser Thr Tyr Ser Leu Ser Ser Thr Leu Thr Leu Ser Lys Ala Asp Tyr
             180                 185                 190

Glu Lys His Lys Val Tyr Ala Cys Glu Val Thr His Gln Gly Leu Ser
         195                 200                 205

Ser Pro Val Thr Lys Ser Phe Asn Arg Gly Glu Cys
         210                 215                 220
```